US011826726B2

(12) United States Patent
Wang et al.

(10) Patent No.: US 11,826,726 B2
(45) Date of Patent: Nov. 28, 2023

(54) ACTIVE ZINC-BASED CATALYST AND PREPARATION METHOD THEREOF, AND USE IN CATALYZING REARRANGEMENT REACTION OF IBUPROFEN

(71) Applicant: Qingdao University of Science and Technology, Qingdao (CN)

(72) Inventors: Yinglong Wang, Qingdao (CN); Peizhe Cui, Qingdao (CN); Zhaoyou Zhu, Qingdao (CN); Fanqing Meng, Qingdao (CN); Xin Li, Qingdao (CN); Jianguang Qi, Qingdao (CN); Limei Zhong, Qingdao (CN); Deping Du, Qingdao (CN); Bingkun Xia, Qingdao (CN); Jianbo Jia, Qingdao (CN); Zuxing Kou, Qingdao (CN)

(73) Assignee: Qingdao University of Science and Technology, Qingdao (CN)

( * ) Notice: Subject to any disclaimer, the term of this patent is extended or adjusted under 35 U.S.C. 154(b) by 7 days.

(21) Appl. No.: 17/860,405

(22) Filed: Jul. 8, 2022

(65) Prior Publication Data

US 2023/0311096 A1    Oct. 5, 2023

(30) Foreign Application Priority Data

Feb. 11, 2022  (CN) .......................... 202210126765.4

(51) Int. Cl.
*B01J 23/06* (2006.01)
*B01J 20/20* (2006.01)
(Continued)

(52) U.S. Cl.
CPC ............... *B01J 23/06* (2013.01); *B01J 20/20* (2013.01); *B01J 35/0013* (2013.01);
(Continued)

(58) Field of Classification Search
CPC ........ B01J 23/06; B01J 20/20; B01J 37/0217; B01J 37/0228; B01J 37/0236; B01J 37/088; B01J 35/06
See application file for complete search history.

(56) References Cited

U.S. PATENT DOCUMENTS

| 4,772,455 A | * | 9/1988 | Izumi | ..................... B01D 53/02 423/239.1 |
| 2009/0080142 A1 | * | 3/2009 | Nanba | ..................... H01G 11/34 502/402 |

(Continued)

FOREIGN PATENT DOCUMENTS

| CN | 105413672 A | * | 3/2016 | ............. B01J 23/06 |
| CN | 108452767 A | * | 8/2018 | |
| CN | 110586063 A | * | 12/2019 | |

OTHER PUBLICATIONS

Liu et al. (CN 110586063), Machine translation, publication date Dec. 20, 2019.*

(Continued)

*Primary Examiner* — Jun Li
(74) *Attorney, Agent, or Firm* — Dominic A. Frisina; Buckingham, Doolittle & Burroughs LLC (57) ABSTRACT

The present disclosure provides an active zinc-based catalyst and a preparation method thereof, and use in catalyzing a rearrangement reaction of ibuprofen. The active zinc-based catalyst includes a carbon-based fiber material and nano-zinc oxide supported on a fiber surface of the carbon-based fiber material. The active zinc-based catalyst is introduced with the carbon-based fiber material, and the carbon-based fiber material is capable of increasing a specific surface area of the catalyst, thereby improving a dispersion degree of zinc oxide, increasing the number of catalytic active sites, and significantly improving a catalytic activity. Meanwhile, due to a certain mechanical strength, the carbon-based fiber (Continued)

material is capable of improving a mechanical strength of the catalyst, making the catalyst exist stably in ketal fluid, maintaining a stable morphology of the catalyst, and avoiding or inhibiting reduction of the catalytic active sites, thereby ensuring a catalytic stability.

14 Claims, 4 Drawing Sheets

(51) Int. Cl.
    *B01J 37/02*       (2006.01)
    *B01J 37/08*       (2006.01)
    *B01J 37/10*       (2006.01)
    *B01J 35/06*       (2006.01)
    *B01J 35/00*       (2006.01)
    *C07C 51/347*     (2006.01)
    *B01J 35/02*       (2006.01)

(52) U.S. Cl.
    CPC ............. *B01J 35/023* (2013.01); *B01J 35/06* (2013.01); *B01J 37/0217* (2013.01); *B01J 37/0228* (2013.01); *B01J 37/0236* (2013.01); *B01J 37/088* (2013.01); *C07C 51/347* (2013.01)

(56) References Cited

U.S. PATENT DOCUMENTS

| 2015/0229012 | A1* | 8/2015 | Toyoda | H01M 12/08 |
| | | | | 429/405 |
| 2018/0313037 | A1* | 11/2018 | Hayakawa | C08L 63/00 |
| 2021/0254243 | A1* | 8/2021 | Ryu | D06M 11/76 |

OTHER PUBLICATIONS

Tan et al. (CN108452767), Machine translation, pulication date Aug. 28, 2018.*

Machine translation of CN105413672, publication date Mar. 23, 2016.*

* cited by examiner

ACTIVE ZINC-BASED CATALYST AND PREPARATION METHOD THEREOF, AND USE IN CATALYZING REARRANGEMENT REACTION OF IBUPROFEN

CROSS REFERENCE TO RELATED APPLICATION

This patent application claims the benefit and priority of Chinese Patent Application No. 202210126765.4, filed on Feb. 11, 2022, the disclosure of which is incorporated by reference herein in its entirety as part of the present application.

TECHNICAL FIELD

The present disclosure relates to the technical field of catalyst materials, in particular to an active zinc-based catalyst and a preparation method thereof, and use in catalyzing a rearrangement reaction of ibuprofen.

BACKGROUND ART

As a non-steroidal anti-inflammatory drug, ibuprofen has anti-inflammatory and analgesic effects that are 16-32 times stronger than aspirin, and has an antipyretic effect which is similar but more durable compared to that of the aspirin, with an average antipyretic effect of 4 h to 6 h. In addition, the ibuprofen has fewer and milder adverse reactions than the aspirin, with no obvious side effects on hematopoietic systems such as liver, kidney, and platelets. Ibuprofen has been widely used in treating rheumatic arthritis, rheumatoid arthritis, osteoarthritis, ankylosing spondylitis, neuritis, pharyngitis, and bronchitis. At present, the ibuprofen is commonly synthesized by a 1,2-translocation rearrangement method of aryl groups. The method includes: conducting Friedel-Crafts acylation on isobutylbenzene as a starting material with 2-chloropropionyl chloride under catalysis of anhydrous aluminum trichloride, to obtain a product; conducting ketalization on the product with neopentyl glycol under catalysis of dilute sulfuric acid to obtain ketal, and subjecting the ketal to 1,2-translocation catalytic rearrangement of aryl groups, followed by conducting hydrolysis and acidification to obtain the ibuprofen. A reaction formula is shown as follows:

During the 1,2-translocation catalytic rearrangement of aryl groups on the ketal (referred to as a rearrangement reaction of ibuprofen), a traditional catalyst is zinc oxide; however, as a catalyst, the zinc oxide reacts violently to easily cause temperature runaway on a reactor, resulting in coked products with a low qualification rate.

SUMMARY

In view of this, an objective of the present disclosure is to provide an active zinc-based catalyst and a preparation method thereof, and use in catalyzing a rearrangement reaction of ibuprofen. The active zinc-based catalyst is capable of catalyzing the rearrangement reaction of the ibuprofen, with mild conditions, a low possibility of temperature runaway, a high catalytic activity, and a desirable stability.

To achieve the above objective, the present disclosure provides the following technical solutions.

The present disclosure provides an active zinc-based catalyst, including a carbon-based fiber material and nano-zinc oxide supported on a fiber surface of the carbon-based fiber material, where the active zinc-based catalyst has 5% to 25% of Zn by mass content.

Preferably, the carbon-based fiber material may include one or more selected from the group consisting of an activated carbon fiber, an activated carbon felt, and a biomass carbon fiber, and may have a fiber diameter of 10 μm to 25 μm.

The present disclosure further provides a preparation method of the active zinc-based catalyst, including the following steps:

(1) immersing the carbon-based fiber material in an aqueous sodium hydroxide solution for activation to obtain a pretreated carbon-based fiber material;

(2) dipping the pretreated carbon-based fiber material in an aqueous solution of a zinc source, and drying to obtain a carbon-based fiber material containing a zinc seed layer;

(3) mixing the carbon-based fiber material containing a zinc seed layer with an alkali source and water to conduct a hydrothermal reaction, and drying an obtained hydrothermal reaction product to obtain a catalyst precursor; and (4) subjecting the catalyst precursor to high-temperature activation at 300° C. to 500° C. under oxygen-free conditions to obtain the active zinc-based catalyst.

Preferably, in step (1), the aqueous sodium hydroxide solution may have a mass concentration of 0.1% to 5%; the activation may be conducted for 2 h to 10 h.

Preferably, in step (2), the zinc source may include one or more selected from the group consisting of zinc acetate, zinc nitrate, and zinc chloride; the aqueous solution of the zinc source may have a concentration of 0.1 mol/L to 5 mol/L;

and the dipping may be conducted 3 to 5 times for 24 h each time, and drying may be conducted after each dipping at 50° C.

Preferably, in step (3), the alkali source may be selected from the group consisting of sodium hydroxide and hexamethylenetetramine; and the alkali source and the zinc source supported on the carbon-based fiber material containing a zinc seed layer may have a molar ratio of (2-16):1.

Preferably, in step (3), the hydrothermal reaction may be conducted at 100° C. to 180° C. for 6 h to 12 h; and the drying may be conducted at 50° C. to 100° C. for 6 h to 12 h.

Preferably, in step (3), the aqueous solution of a zinc source may be used as an inducer during the mixing.

Preferably, in step (4), the high-temperature activation may be conducted for 4 h to 6 h.

The present disclosure further provides use of the active zinc-based catalyst or an active zinc-based catalyst prepared by the preparation method in catalyzing a rearrangement reaction of ibuprofen.

The present disclosure provides an active zinc-based catalyst, including a carbon-based fiber material and nano-zinc oxide supported on a fiber surface of the carbon-based fiber material; where the active zinc-based catalyst has 5% to 25% of Zn by mass content. The active zinc-based catalyst is introduced with the carbon-based fiber material, and the carbon-based fiber material is capable of increasing a specific surface area of the catalyst, thereby improving a dispersion degree of zinc oxide, increasing the number of catalytic active sites, avoiding catalyst agglomeration, and significantly improving a catalytic activity of the catalyst. In addition, the carbon-based fiber material has fiber voids that are conducive to the diffusion of ibuprofen esters, a product of the rearrangement reaction of ibuprofen, thereby improving a catalytic selectivity and reducing the occurrence of side reactions. Meanwhile, due to a certain mechanical strength of the carbon-based fiber material, the mechanical strength of the catalyst is improved, making the catalyst exist stably in ketal fluid, maintaining a stable morphology of the catalyst, and avoiding or inhibiting reduction of the catalytic active sites, thereby ensuring a catalytic stability. Furthermore, the carbon-based fiber material is conducive to liquid agitation during the reaction, and has a high mass transfer rate to promote rapid heat dissipation, thus dispersing heat generated by the reaction to avoid temperature runaway. The fiber voids of carbon-based fiber material make a temperature difference of a catalyst bed easy to control, achieving high catalyst selectivity. The active zinc-based catalyst is capable of catalyzing the rearrangement reaction of the ibuprofen, with mild conditions, a low possibility of temperature runaway, a high catalytic activity, and a desirable stability.

DETAILED DESCRIPTION OF THE EMBODIMENTS

The present disclosure provides an active zinc-based catalyst, including a carbon-based fiber material and nano-zinc oxide supported on a fiber surface of the carbon-based fiber material; where the active zinc-based catalyst has 5% to 25% of Zn by mass content.

In the present disclosure, the carbon-based fiber material includes preferably one or more selected from the group consisting of an activated carbon fiber, an activated carbon felt, and a biomass carbon fiber, and has a fiber diameter of preferably 10 μm to 25 μm; and the biomass carbon fiber is preferably one or more selected from the group consisting of a cotton fiber, poplar floccule and catkin. The active zinc-based catalyst has 5% to 25% of Zn by mass content.

The active zinc-based catalyst is introduced with the carbon-based fiber material, and the carbon-based fiber material is capable of increasing a specific surface area of the catalyst, thereby improving a dispersion degree of zinc oxide, increasing the number of catalytic active sites, and significantly improving a catalytic activity. Meanwhile, due to a certain mechanical strength, the carbon-based fiber material is capable of improving a mechanical strength of the catalyst, making the catalyst exist stably in ketal fluid, maintaining a stable morphology of the catalyst, and avoiding or inhibiting reduction of the catalytic active sites, thereby ensuring a catalytic stability.

The present disclosure further provides a preparation method of the active zinc-based catalyst, including the following steps:

(1) immersing the carbon-based fiber material in an aqueous sodium hydroxide solution for activation to obtain a pretreated carbon-based fiber material;

(2) dipping the pretreated carbon-based fiber material in an aqueous solution of a zinc source, and drying to obtain a carbon-based fiber material containing a zinc seed layer;

(3) mixing the carbon-based fiber material containing a zinc seed layer with an alkali source and water to conduct a hydrothermal reaction, and drying an obtained hydrothermal reaction product to obtain a catalyst precursor; and (4) subjecting the catalyst precursor to high-temperature activation at 300° C. to 500° C. under oxygen-free conditions to obtain the active zinc-based catalyst.

In the present disclosure, the carbon-based fiber material is immersed in the aqueous sodium hydroxide solution for activation to obtain the pretreated carbon-based fiber material. In the present disclosure, the carbon-based fiber material is the same as that in the above technical solution; and there is no special requirement for a source of the carbon-based fiber material, and commercially-available products well known to those skilled in the art can be used. Before the activation, the carbon-based fiber material is preferably washed and dried in sequence; the washing includes acetone washing, ethanol washing, and water washing in sequence; there is no special requirement for the number of washing times, as long as stains and impurities on a surface of the carbon-based fiber material can be cleaned; and there is no special requirement for a temperature and time of the drying, as long as water on a carbon fiber surface after washing can be fully removed. The aqueous sodium hydroxide solution has a mass concentration of preferably 0.1% to 5%, more preferably 3% to 5%; and the activation is conducted for preferably 2 h to 10 h, more preferably 2 h to 5 h. A surface of the carbon-based fiber material is extremely smooth; the carbon-based fiber material is immersed in the aqueous sodium hydroxide solution, to further soften the surface of the carbon-based fiber material, such that the surface of the carbon-based fiber material is roughened, facilitating subsequent supporting of the active zinc. After the activation, an obtained fiber product is further preferably washed and dried in sequence to obtain a pretreated carbon fiber.

In the present disclosure, the pretreated carbon-based fiber material is dipped in the aqueous solution of the zinc source, and dried to obtain the carbon-based fiber material containing a zinc seed layer. In the present disclosure, the zinc source includes preferably one or more selected from the group consisting of zinc acetate, zinc nitrate, and zinc chloride; in an example, the zinc source is selected from the group consisting of zinc acetate dihydrate and zinc nitrate hexahydrate; the aqueous solution of the zinc source has a concentration of preferably 0.1 mol/L to 5 mol/L, more preferably 0.1 mol/L to 3 mol/L. Specifically, a dipping method preferably includes: adding the pretreated carbon-based fiber material into the aqueous solution of the zinc source, conducting a ultrasonic treatment for preferably 2 h to remove air bubbles on the surface of the carbon-based fiber material, and dipping. The dipping is conducted preferably 3 to 5 times for preferably 24 h each time, and drying is conducted after each dipping at preferably 50° C., that is, dipping-drying is conducted repeatedly.

In the present disclosure, the carbon-based fiber material containing a zinc seed layer is mixed with the alkali source and water to conduct the hydrothermal reaction, and the obtained hydrothermal reaction product is dried to obtain the catalyst precursor. The alkali source is preferably sodium hydroxide or hexamethylenetetramine, which is used to convert the zinc source supported on the carbon-based fiber material containing a zinc seed layer into zinc hydroxide; and the alkali source and the zinc source supported on the carbon-based fiber material containing a zinc seed layer have a molar ratio of preferably (2-16):1, more preferably (4-8):1. The mixing further includes preferably adding an inducer; the inducer is preferably the aqueous solution of the zinc source, and the zinc source in the aqueous solution of the zinc source includes preferably one or more selected from the group consisting of the zinc acetate, the zinc nitrate, and the zinc chloride, more preferably the same as that in the carbon-based fiber material containing a zinc seed layer; the aqueous solution of the zinc source has a concentration preferably the same as that of the aqueous solution of the zinc source in the above technical solution; and the inducer and the carbon-based fiber material have a liquid-to-material ratio of preferably 10 mL:1 g. The hydrothermal reaction is conducted at preferably 100° C. to 180° C., more preferably 140° C. to 180° C. for preferably 6 h to 12 h, more preferably 8 h to 12 h. The hydrothermal reaction specifically includes preferably: dissolving the alkali source in water to obtain an aqueous alkali source solution; adding the inducer to the carbon-based fiber material containing a zinc seed layer for standing, and adding the aqueous alkali source solution to an obtained material for stirring; placing a mixed material obtained by stirring in a hydrothermal kettle, and conducting the hydrothermal reaction at 100° C. to 180° C. to obtain the hydrothermal reaction product. The aqueous alkali source solution has a concentration of preferably 0.2 mol/L; the standing is conducted for preferably 24 h, and the stirring is conducted at preferably 800 rpm to 1200 rpm for preferably 1 h. During the hydrothermal reaction, the zinc source on the surface of the carbon-based fiber material containing a zinc seed layer reacts with sodium hydroxide to form zinc hydroxide. The hydrothermal reaction product is preferably naturally cooled to room temperature and dried; the drying is conducted at preferably 50° C. to 100° C., more preferably 70° C. to 80° C. for preferably 6 h to 12 h, more preferably 10 h to 12 h; free water on a surface of the hydrothermal reaction product is removed by the drying to obtain the catalyst precursor.

In the present disclosure, the catalyst precursor is subjected to high-temperature activation under oxygen-free conditions to obtain the active zinc-based catalyst. The oxygen-free conditions are preferably a nitrogen atmosphere. The high-temperature activation is conducted at 300° C. to 500° C., preferably 350° C. to 450° C. for preferably 4 h to 6 h, more preferably 4 h to 5.5 h. During the high-temperature activation, the zinc hydroxide in the catalyst precursor removes lattice water and is converted into zinc oxide; temperature and time of the high-temperature activation are strictly controlled to avoid carbon fiber breakage. After the high-temperature activation, an activated product is preferably naturally cooled to room temperature to obtain the active zinc-based catalyst.

The present disclosure further provides use of the active zinc-based catalyst or an active zinc-based catalyst prepared by the preparation method in catalyzing a rearrangement reaction of ibuprofen (subjecting ketal to 1,2-translocation catalytic rearrangement of aryl groups to form ibuprofen esters). In the present disclosure, the active zinc-based catalyst is preferably packed in a fixed bed, and has a loading amount of preferably 0.6% to 1% of a volume of the fixed bed; the ketal has a feed rate of preferably 1,000 L/h to 1,500 L/h, and has a residence time in the fixed bed of preferably 20 min to 60 min; the rearrangement reaction of ibuprofen is conducted at preferably 100° C. to 180° C. The active zinc-based catalyst is capable of catalyzing the rearrangement reaction of the ibuprofen, with mild conditions, a low possibility of temperature runaway, a high catalytic activity, and a desirable stability. In addition, the active zinc-based catalyst does not contain chloride ions and is less corrosive to equipment; there is no need to dissolve the catalyst with an organic solvent during use, avoiding a complicated recovery process of the organic solvent; in addition, the active zinc-based catalyst is a solid catalyst loaded in the fixed bed, which can continuously conduct catalysis to improve production efficiency.

The active zinc-based catalyst and the preparation method thereof, and the use in catalyzing a rearrangement reaction of ibuprofen provided by the present disclosure will be described in detail below with reference to examples, but these examples should not be construed as limiting the scope of the present disclosure.

Example 1

1 g of a biomass carbon fiber material (absorbent cotton fiber, with a fiber diameter of 10 μm) was repeatedly washed with acetone and an ethanol solution for several times, and then with deionized water for the last time, dried in a drying box fully, and immersed in a 5 wt % sodium hydroxide solution for activation for 2 h to obtain a pretreated carbon fiber.

2.1951 g of zinc acetate dihydrate was dissolved with 100 mL of deionized water to prepare a zinc acetate aqueous solution with a concentration of 0.1 mol/L; the pretreated carbon fiber was immersed in the zinc acetate aqueous solution, air bubbles on a surface of the carbon fiber were removed by ultrasonic treatment (for about 2 h) and then stayed for 24 h, and the carbon fiber was dried in a drying oven at 50° C.; a dipping-drying operation was repeated 3 times to obtain a biomass carbon fiber containing a zinc seed layer, where the zinc acetate had a loading amount of 0.001 mol.

A dried carbon fiber containing a zinc seed layer was added to 10 mL of the zinc acetate aqueous solution, and allowed to stand for 24 h; 40 mL of an aqueous sodium hydroxide solution with a concentration of 0.2 mol/L was added, a mixed solution was vigorously stirred for 1 h and reacted in a 100 mL hydrothermal kettle at 180° C. for 12 h, and a reaction product was naturally cooled to room temperature; a cooled material was dried in a drying oven at 80° C. for 6 h to obtain a catalyst precursor.

The catalyst precursor was activated in a tubular heating furnace at 450° C. for 4 h under an $N_2$ atmosphere, and cooled to room temperature naturally to obtain an active zinc-based catalyst, where the catalyst had 24% of Zn.

Figure 1:
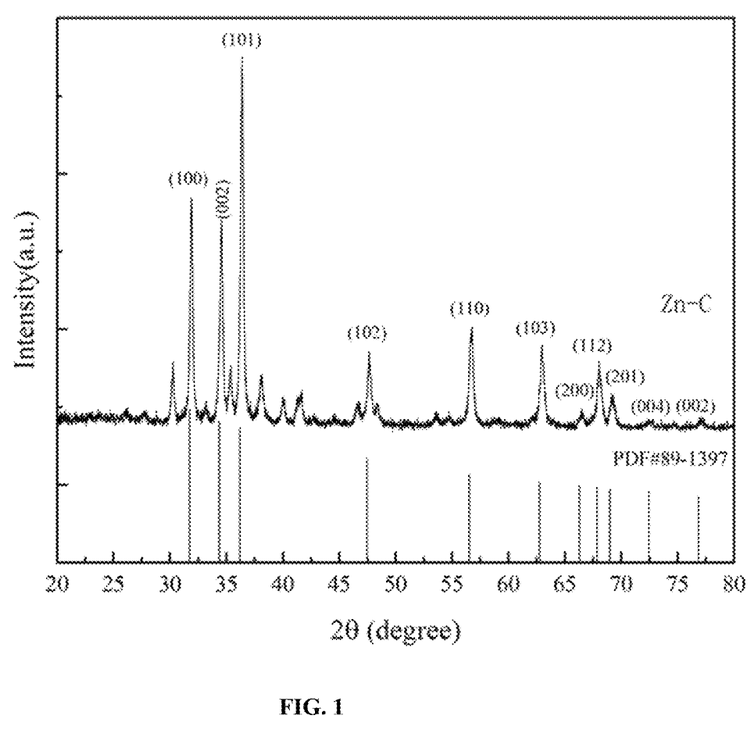
FIG. 1 shows an X-ray diffraction (XRD) pattern of an active zinc-based catalyst prepared in Example 1.

FIG. 1 shows an XRD pattern of the active zinc-based catalyst. The XRD pattern in FIG. 1 confirms that all diffraction peaks can be assigned to hexagonal wurtzite (space group: P63mc (186) a=3.250 nm, b=3.250 nm, c=5.207 nm).

Figure 2:
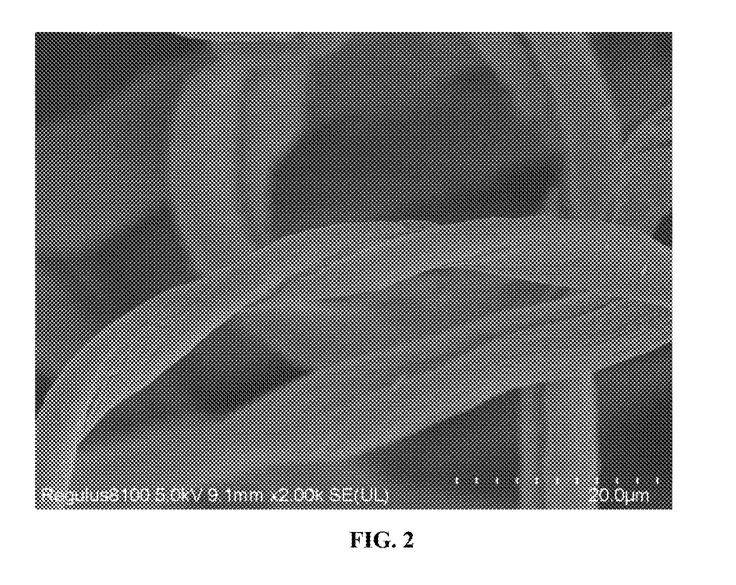
FIG. 2 shows a scanning electron microscope (SEM) photograph of a biomass carbon fiber in Example 1.
Figure 3:
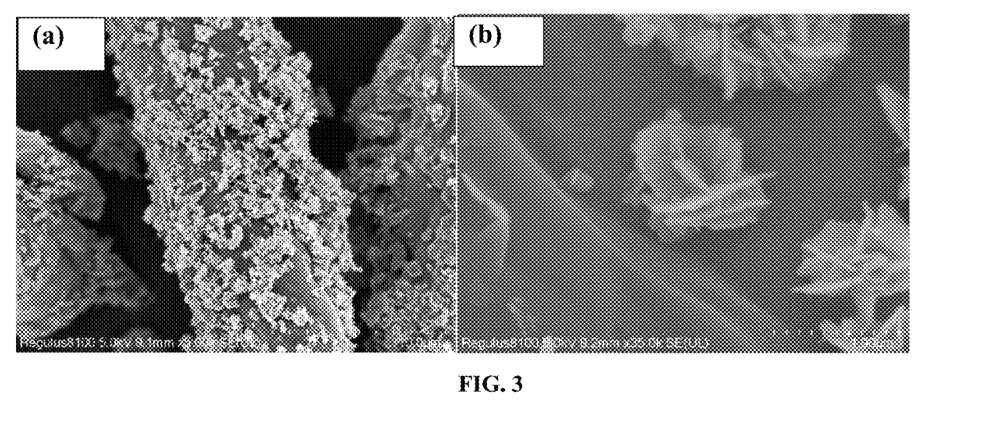
FIG. 3 shows a SEM photograph of the active zinc-based catalyst prepared in Example 1 and an amplified SEM photograph of active zinc in the catalyst, where (a) shows the SEM photograph of the active zinc-based catalyst, and (b) shows the amplified SEM photograph of active zinc in the catalyst.

FIG. 2 shows a SEM photograph of the biomass carbon fiber; it can be seen that the biomass carbon fiber is a typical spiral fiber with a smooth surface. FIG. 3 shows a SEM photograph of the active zinc-based catalyst prepared in Example 1 and an amplified SEM photograph of active zinc in the catalyst, where (a) shows the SEM photograph of the active zinc-based catalyst, and (b) shows the amplified SEM photograph of active zinc in the catalyst. It can be seen from FIG. 3 that flower-like ZnO grows on the fiber, with a width of 285 nm to 420 nm; the active zinc-based catalyst exhibits a densely-supported packing structure.

Comparative Example 1

Zinc oxide is used as a catalyst.

Comparative Example 2

Zinc ibuprofen is used as a catalyst.

Comparative Example 3

Zinc chloride is used as a catalyst.

The catalysts of Example 1 and Comparative Examples 1 to 3 were used to catalyze a rearrangement reaction of ibuprofen to conduct a catalytic performance test. A test method included: the catalyst was packed into a fixed bed, with a filling amount of 0.8% of the whole fixed bed; the fixed bed was preheated by introducing steam to 150° C.; a feed pump was started to make feed liquid enter the bed, a ketal feed rate was controlled to 1,200 L/h, and a ketal residence time in the bed was set to 20 min. After the reaction, the catalyst was removed from the fixed bed, and repeatedly washed with ethanol and deionized water to remove impurities on a surface of the catalyst; the catalyst was dried, and placed in the fixed bed to repeat the rearrangement reaction of ibuprofen, for 4 times altogether (that is, the rearrangement reaction of ibuprofen was conducted 5 times in total).

Figure 4:
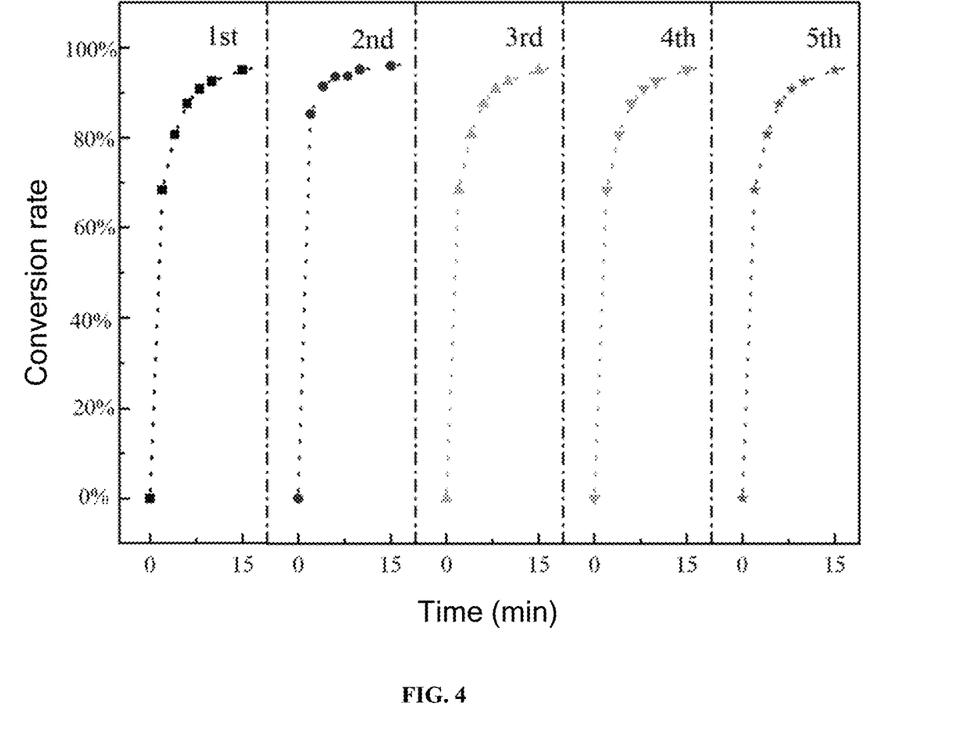
FIG. 4 shows a catalytic cycle effect of the active zinc-based catalyst prepared in Example 1.
Figure 5:
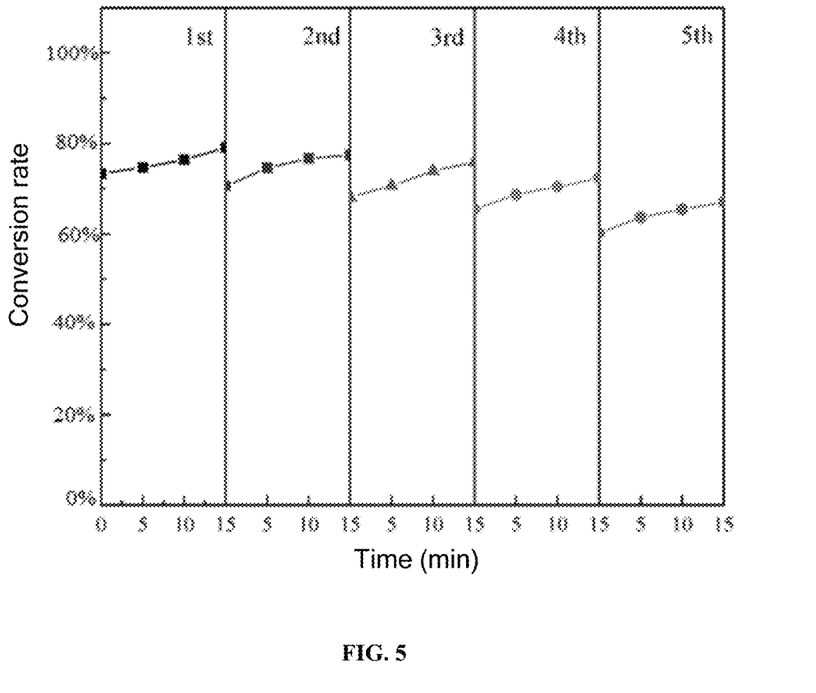
FIG. 5 shows a catalytic cycle effect of a zinc oxide-based catalyst prepared in Comparative Example 1.
Figure 6:
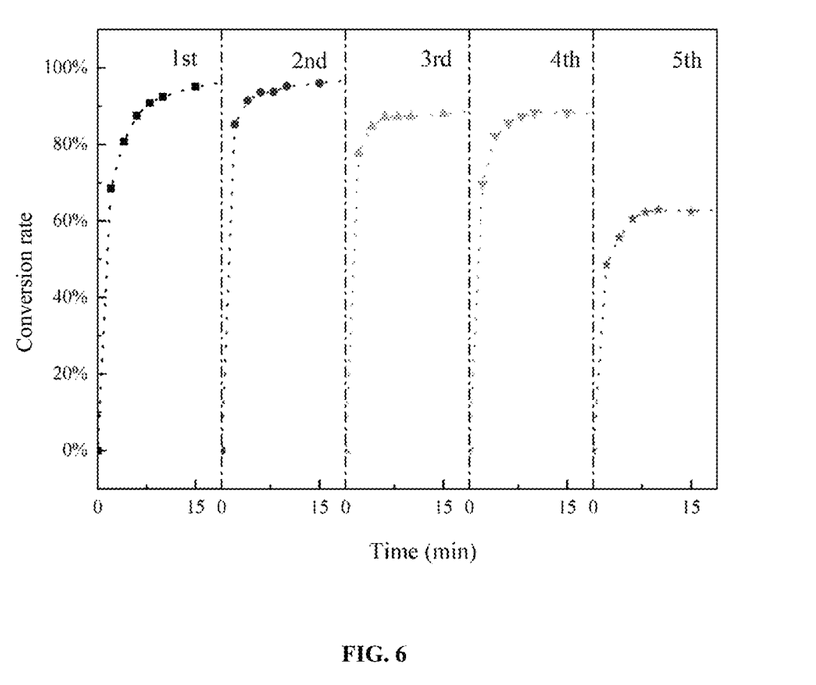
FIG. 6 shows a catalytic cycle effect of a zinc ibuprofen-based catalyst prepared in Comparative Example 2.
Figure 7:
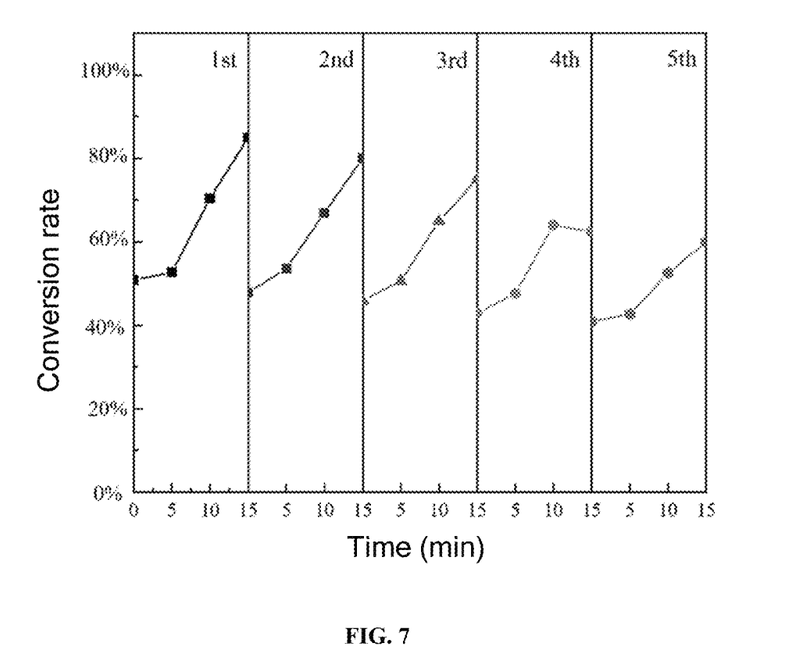
FIG. 7 shows a catalytic cycle effect of a zinc chloride-based catalyst prepared in Comparative Example 3.

FIG. 4 shows a catalytic cycle effect of the active zinc-based catalyst prepared in Example 1; FIG. 5 shows a catalytic cycle effect of the zinc oxide-based catalyst prepared in Comparative Example 1; FIG. 6 shows a catalytic cycle effect of the zinc ibuprofen-based catalyst prepared in Comparative Example 2; and FIG. 7 shows a catalytic cycle effect of the zinc chloride-based catalyst prepared in Comparative Example 3. It can be seen from the comparison of FIG. 4 (active zinc-based catalyst) and FIG. 6 (zinc ibuprofen-based catalyst) that in the first cycle, the two have an almost same conversion rate; however, with an increase of the number of cycles, the zinc ibuprofen-based catalyst has a conversion rate decreased significantly, which is 65.6% after the fifth cycle; while the active zinc-based catalyst can still maintain a high conversion rate of more than 97.7%. Comparing FIG. 5 (zinc oxide-based catalyst) and FIG. 7 (zinc chloride-based catalyst) with FIG. 4 (active zinc-based catalyst), it can be clearly seen that during the first use, the zinc chloride-based catalyst has a conversion rate of 85.6%, and the zinc oxide-based catalyst has a conversion rate of 79.2%, which are almost the same but far lower than the zinc ibuprofen-based catalyst and the active zinc-based catalyst, and show a significant decrease with an increase of the number of cycles.

Example 2

1 g of an activated carbon felt material (with a fiber diameter of 14 μm) was cut into small pieces and washed several times with acetone and an ethanol solution, and then with deionized water for the last time, dried in a drying box fully, and immersed in a 5 wt % sodium hydroxide solution for activation for 2 h to obtain a pretreated activated carbon felt.

2.97 g of zinc nitrate hexahydrate was dissolved with 100 mL of deionized water to prepare a zinc nitrate aqueous solution with a concentration of 0.1 mol/L; the pretreated activated carbon felt was immersed in the zinc nitrate aqueous solution, air bubbles on a surface of the carbon felt were removed by ultrasonic treatment (for about 2 h) and then stayed for 24 h, and the carbon felt was dried in a drying oven at 50° C.; a dipping-drying operation was repeated 3 times to obtain a carbon felt containing a zinc seed layer, where the zinc nitrate had a loading amount of 0.001 mol.

A dried carbon felt containing a zinc seed layer was added to 10 mL of the zinc nitrate aqueous solution, and allowed to stand for 24 h; 40 mL of a hexamethylenetetramine aqueous solution with a concentration of 0.2 mol/L was added, a mixed solution was vigorously stirred for 24 h and reacted in a 100 mL hydrothermal kettle at 140° C. for 6 h, and a reaction product was naturally cooled to room temperature; a cooled material was dried in a drying oven at 80° C. for 6 h to obtain a catalyst precursor.

The catalyst precursor was activated in a tubular heating furnace at 450° C. for 5 h under an $N_2$ atmosphere, and cooled to room temperature naturally to obtain an active zinc-based catalyst, where the catalyst had 15% of Zn.

Figure 8:
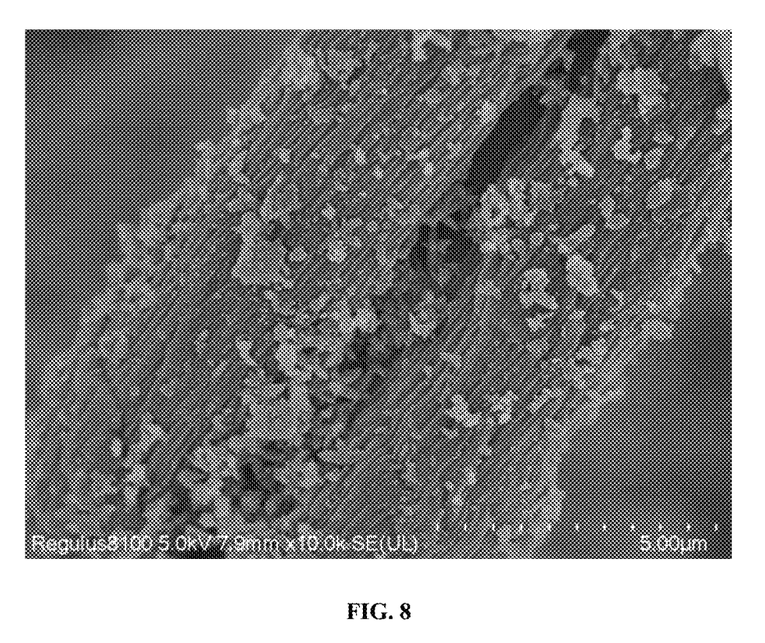
FIG. 8 shows a SEM photograph of an active zinc-based catalyst prepared in Example 2.

FIG. 8 shows a SEM photograph of the active zinc-based catalyst prepared in Example 2.

The active zinc-based catalyst prepared in Example 2 was used to catalyze a rearrangement reaction of ibuprofen to conduct a catalytic performance test. The test results are that the active zinc-based catalyst prepared in Example 2 has a catalytic effect similar to that in Example 1, which also has a higher catalytic activity and catalytic cycle stability.

As can be seen from the above examples, the active zinc-based catalyst provided by the present disclosure can used for catalyzing the rearrangement reaction of ibuprofen, with a high catalytic activity and desirable stability.

The above descriptions are merely preferred implementations of the present disclosure. It should be noted that a person of ordinary skill in the art may further make several improvements and modifications without departing from the principle of the present disclosure, but such improvements and modifications should be deemed as falling within the protection scope of the present disclosure.

What is claimed is:

1. A preparation method of a zinc oxide-containing catalyst, comprising the following steps:
   (1) immersing a carbon fiber material in an aqueous sodium hydroxide solution for a first activation to obtain a pretreated carbon fiber material;
   (2) dipping the pretreated carbon fiber material in a first aqueous solution of a zinc salt, and drying to obtain a carbon fiber material containing a zinc seed layer, wherein the zinc seed layer is the zinc salt; wherein the zinc salt comprises one or more selected from the group consisting of zinc acetate, zinc nitrate, and zinc chloride; the aqueous zinc salt has a concentration of 0.1 mol/L to 5.0 mol/L; and the dipping is conducted for 3 to 5 times for 24 h each time, and drying is conducted after each dipping at 50° C.;
   (3) mixing the carbon fiber material containing a zinc seed layer with an alkali source and water to conduct a hydrothermal reaction, and drying an obtained hydrothermal reaction product to obtain a catalyst precursor containing zinc hydroxide wherein the alkali source is selected from the group consisting of sodium hydroxide and hexamethylenetetramine; and
   (4) subjecting the catalyst precursor to a second activation at 300° C. to 500° C. under oxygen-free conditions to obtain the zinc oxide-containing catalyst, wherein the zinc oxide-containing catalyst comprises the carbon fiber material and nano-zinc oxide supported on a fiber surface of the carbon fiber material, and the zinc oxide-containing catalyst has 5% to 25% of Zn by mass content.

2. The preparation method according to claim 1, wherein the carbon fiber material comprises one or more selected from the group consisting of an activated carbon fiber, an activated carbon felt, and a biomass carbon fiber, and has a fiber diameter of 10 μm to 25 μm.

3. The preparation method according to claim 1, wherein in step (1), the aqueous sodium hydroxide solution has a mass concentration of 0.1% to 5%; and the first activation is conducted for 2 h to 10 h.

4. The preparation method according to claim 2, wherein in step (1), the aqueous sodium hydroxide solution has a mass concentration of 0.1% to 5%; and the first activation is conducted for 2 h to 10 h.

5. The preparation method according to claim 1, wherein in step (3), the alkali source and the zinc salt supported on the carbon fiber material containing a zinc seed layer have a molar ratio of (2-16):1.

6. The preparation method according to claim 2, wherein in step (3), the alkali source is selected from the group consisting of sodium hydroxide and hexamethylenetetramine; and the alkali source and the zinc salt supported on the carbon fiber material containing a zinc seed layer have a molar ratio of (2-16):1.

7. The preparation method according to claim 1, wherein in step (3), the hydrothermal reaction is conducted at 100° C. to 180° C. for 6 h to 12 h; and the drying is conducted at 50° C. to 100° C. for 6 h to 12 h.

8. The preparation method according to claim 2, wherein in step (3), the hydrothermal reaction is conducted at 100° C. to 180° C. for 6 h to 12 h; and the drying is conducted at 50° C. to 100° C. for 6 h to 12 h.

9. The preparation method according to claim 5, wherein in step (3), the hydrothermal reaction is conducted at 100° C. to 180° C. for 6 h to 12 h; and the drying is conducted at 50° C. to 100° C. for 6 h to 12 h.

10. The preparation method according to claim 6, wherein in step (3), the hydrothermal reaction is conducted at 100° C. to 180° C. for 6 h to 12 h; and the drying is conducted at 50° C. to 100° C. for 6 h to 12 h.

11. The preparation method according to claim 1, wherein in step (3), a second aqueous solution of a zinc salt is added as an inducer during the mixing.

12. The preparation method according to claim 2, wherein in step (3), a second aqueous solution of a zinc salt is added as an inducer during the mixing.

13. The preparation method according to claim 1, wherein in step (4), the second activation is conducted for 4 h to 6 h.

14. The preparation method according to claim 2, wherein in step (4), the second activation is conducted for 4 h to 6 h.

* * * * *